United States Patent [19]

Kelman

[11] Patent Number: 5,154,694
[45] Date of Patent: Oct. 13, 1992

[54] TISSUE SCRAPER DEVICE FOR MEDICAL USE

[76] Inventor: Charles D. Kelman, 721 Fifth Ave., New York, N.Y. 10022

[21] Appl. No.: 668,341

[22] Filed: Mar. 8, 1991

Related U.S. Application Data

[63] Continuation of Ser. No. 362,066, Jun. 6, 1989, abandoned.

[51] Int. Cl.⁵ .............................. A61B 17/32
[52] U.S. Cl. .................................. 604/22; 604/27; 604/35; 606/107; 606/169; 606/171
[58] Field of Search ............. 606/107, 167, 171; 128/24 AA; 604/22, 27, 35

[56] References Cited

U.S. PATENT DOCUMENTS

| | | | |
|---|---|---|---|
| 3,589,363 | 6/1971 | Banko et al. | 604/22 |
| 3,794,040 | 2/1974 | Balamuth | 606/27 |
| 4,136,700 | 1/1979 | Broadwin et al. | 604/22 |
| 4,301,802 | 11/1981 | Poler | 604/22 |
| 4,674,500 | 6/1987 | DeSatnick | 604/22 |
| 4,750,488 | 6/1988 | Wuchinich | 604/22 |
| 4,832,683 | 5/1989 | Idemoto et al. | 604/22 |

*Primary Examiner*—David M. Shay
*Attorney, Agent, or Firm*—Darby & Darby

[57] ABSTRACT

Tissue scraper element for medical use in extracting undesired body tissue, e.g. a natural eye lens, by mechanical vibratory contact to disintegrate the tissue and by accompanying flushing fluid flow removal of the disintegrated tissue from the tissue site, the element including a longitudinal shank whose base end in use is mounted on a hand held instrument for longitudinal back and forth vibratory movement, and whose free end terminates in a tip extending crosswise of the shank longitudinal axis. The shank has an internal flow passage, and the tip terminates in a laterally outwardly directed scraper edge and has an internal flow channel communicating the shank passage with a mouth adjacent the scraper edge. Upon contacting the scraper edge against the undesired tissue in a direction crosswise of the shaft longitudinal axis, while subjecting the shank and tip to such vibratory movement and accompanying flushing fluid flow via the tip mouth, the tissue will be disintegrated and removed.

10 Claims, 2 Drawing Sheets

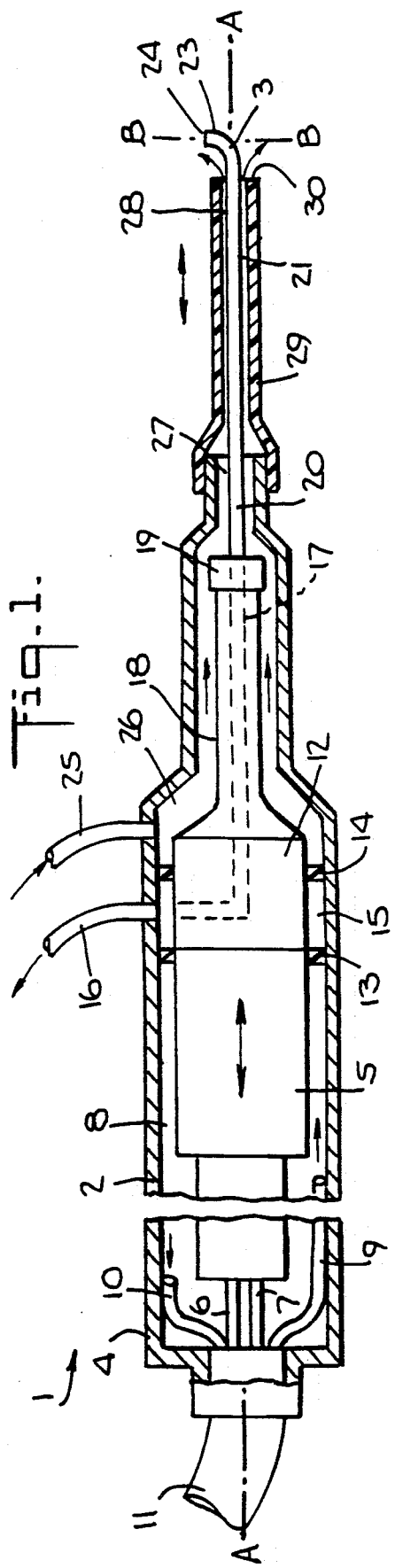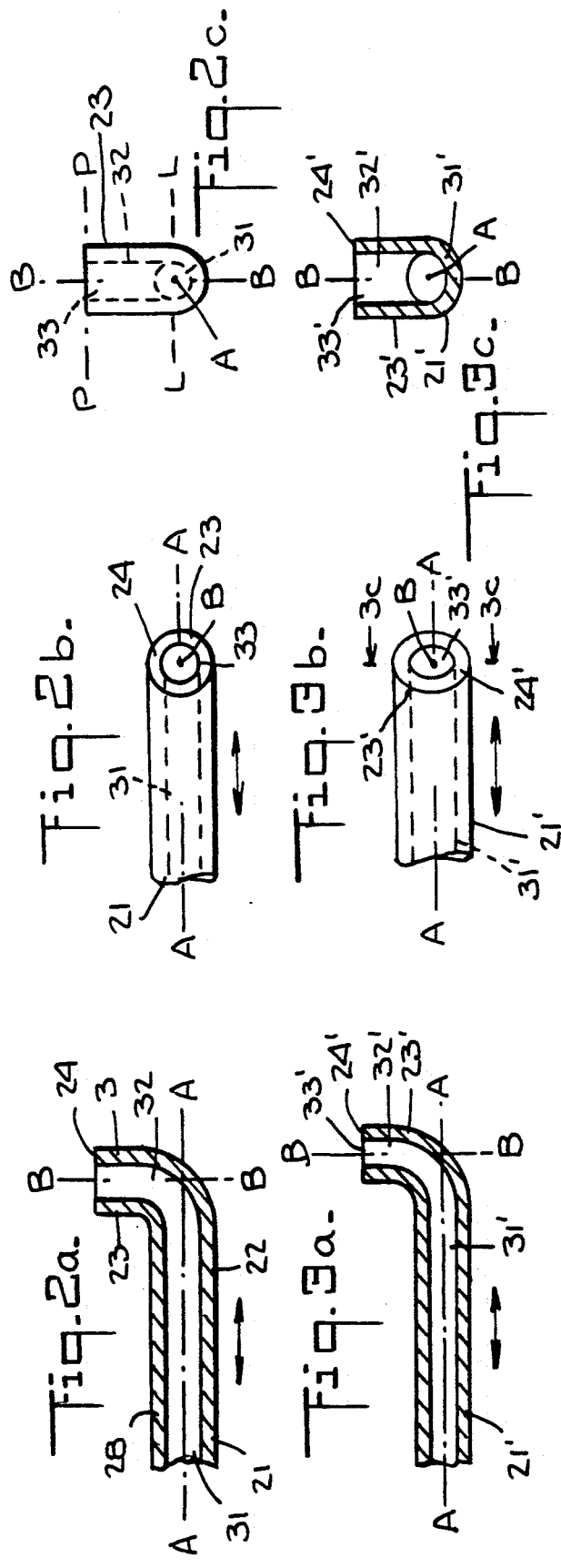

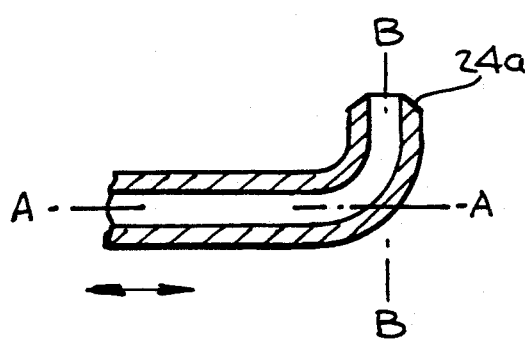
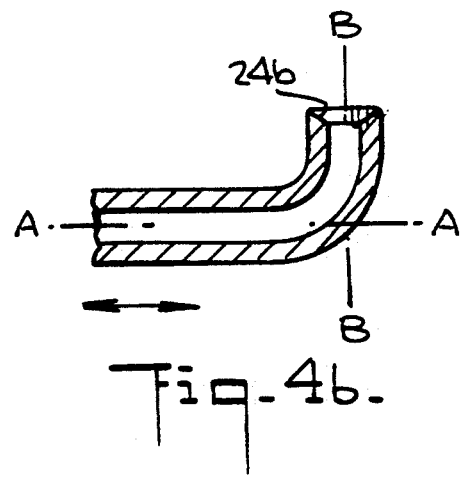
Fig. 4a.  Fig. 4b.
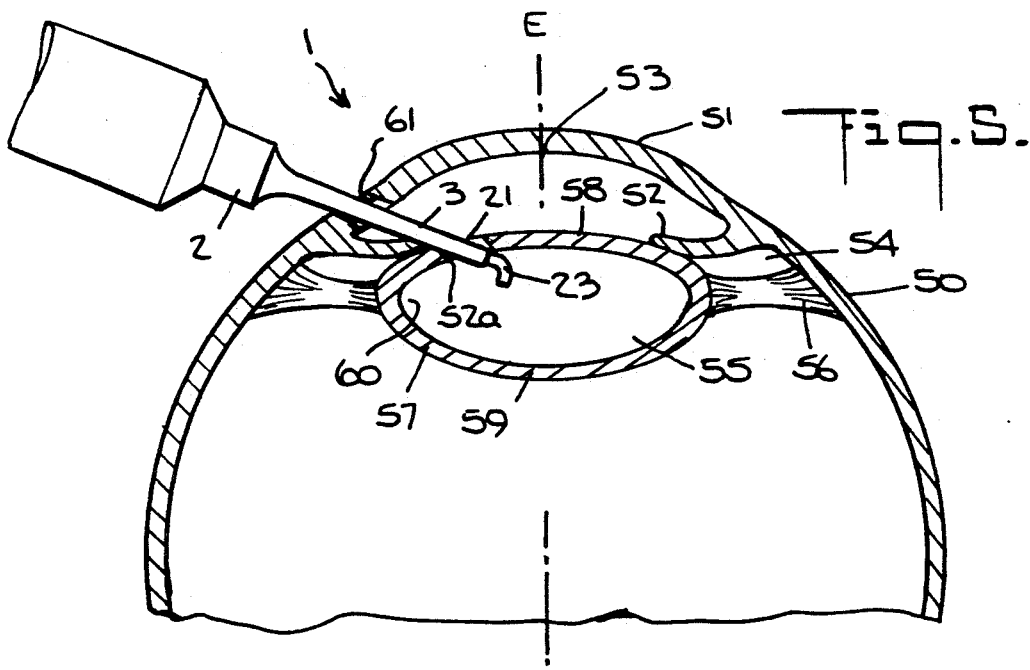
Fig. 5.
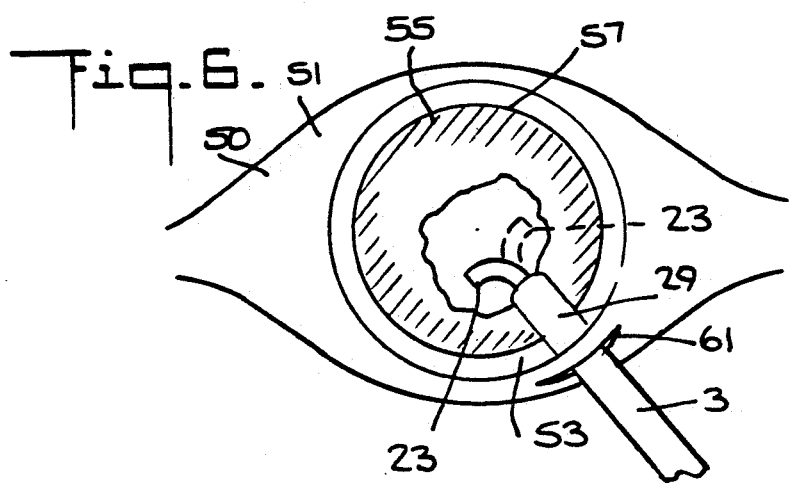
Fig. 6.

TISSUE SCRAPER DEVICE FOR MEDICAL USE

This is a continuation of application Ser. No. 362,066, filed Jun. 6, 1989 now abandoned.

FIELD AND BACKGROUND OF THE INVENTION

The present invention relates to a tissue scraper element for medical use, and more particularly to such an element usable in extracting undesired body tissue, e.g. a cataracted natural eye lens, by mechanical vibratory contact to disintegrate the tissue and by accompanying flushing fluid flow removal of the disintegrated tissue from the tissue site, the element including a shank, mountable on a hand held instrument for longitudinal back and forth vibratory movement, and having a crosswise extending tip terminating in a laterally outwardly directed scraper edge, a flow channel in the tip communicating a flow passage in the shank with a mouth adjacent the scraper edge to accommodate such flushing fluid flow.

U.S. Pat. No. 3,589,363 to Banko and Kelman discloses a hand held instrument and method for breaking apart and removing by flushing fluid flow undesired material such as tissue from a body site. The instrument contains vibratory movement means connected to a longitudinal shank having an axial bore leading to a mouth at its projecting straight tip, and a conduit leading to an opening at the shank exterior, such that axial vibratory movement of the tip, when pressed axially against the tissue, breaks up the tissue by jack-hammer-like action, for removal by flow of fluid from a source to the site via one of the mouth and opening and its return with broken up tissue via the other of the mouth and opening to a suction source.

This patent teaching has been for break up and removal of cataracted eye lens tissue per known surgical procedures. Such procedures are effected through a corneal incision kept as small as possible to minimize patient trauma. In this regard, it is desirable to remove all tissue debris from the posterior capsule.

However, it has been found that in using the straight tip instrument of this patent for such purposes, the procedures is burdened by awkwardness in the positioning of the instrument in the surgeon's hand under the extant vibratory conditions, especially when attempting to break up portions of the cataracted lens tissue in remote portions of the posterior capsule in relation to the fixed position of the necessarily small corneal incision. This awkwardness leads to uncomfortable hand and finger positions of the surgeon when holding the vibrating instrument and manipulating it in relation to that fixed location of the corneal incision for bringing the free end of its straight tip into proper "head-on" position for breaking up the lens tissue in the inherently confined spatial areas involved.

While the instrument of this patent may be provided with a radially extending, sharp pointed projection, this is only used to tear the anterior wall of the capsule covering the lens by back and forth tearing action to obtain access to the lens prior to initiation of the tissue breaking apart procedure. This projection would be of no value in breaking apart the main mass of the lens tissue within its capsule, especially considering that the projection has a pointed end and is positioned with that end remote from the tip mouth through which the flushing fluid flows.

On the other hand, the back and forth jack-hammer-like action of the straight tip of the instrument of this patent, which is used for the actual breaking up of the lens tissue, operates by way of axial or longitudinal direction percussion impulse exerted perpendicularly against the tissue surface as anvil, inherently resulting in a coarse shattering of the tissue.

As a result, the surgeon must take pains to manipulate the tip through many diverse angular positions, while the shank extends through the relatively small incision, to be able to apply the leading transverse face of the longitudinal straight tip in "head-on" relation with the lens tissue, as the very nature of the percussion impulse action is such that the axially vibrating tip makes head-on face-to-face contact with the tissue surface. Also, care must be taken to avoid unduly pressing the tip against the tissue surface of the posterior wall of the capsule for fear of puncturing or otherwise damaging unnecessarily that wall which is intended to remain intact.

It would be desirable to provide an instrument of the type shown in this patent, but which is easier and faster to use and which avoids the aforesaid disadvantages by permitting more efficient breaking apart and flushing removal of the undesired tissue from the treatment site, thus reducing the time required for the surgical procedure of cataracted lens removal while at the same time simplifying the motions which the surgeon must carry out.

SUMMARY OF THE INVENTION

It is among the objects of this invention to provide a tissue scraper element for medical use in extracting undesired body tissue, e.g. the natural eye lens, by mechanical vibratory contact to disintegrate the tissue and by accompanying flushing fluid flow removal of the disintegrated tissue from the tissue site, with the element in use being mounted on a hand held instrument for back and forth vibratory movement in a longitudinal direction but which has an offset tip provided with a scraper edge for contacting the tissue in a direction generally crosswise of the vibratory movement direction, resulting in efficient and uniform extraction of the undesired tissue at minimum patient risk and maximum comfort to the surgeon's hand and fingers.

According to one aspect of this invention, a tissue scraper element is advantageously provided for medical use in extracting undesired body tissue by mechanical vibratory contact to disintegrate the tissue and by accompanying flushing fluid flow removal of the disintegrated tissue from the tissue site.

The tissue scraper element includes a shank extending along a longitudinal axis and having a base end portion adapted to be mounted on a hand held instrument for back and forth vibratory movement of the shank in the direction of its longitudinal axis at a selective amplitude and frequency, and a free end portion terminating in a sidewise offset or bent tip extending along a lateral, preferably radial, axis crosswise of said longitudinal axis.

The shank has an exterior surface and an internal fluid flow passage, and the tip terminates in a laterally, preferably radially, outwardly directed scraper edge spaced laterally, preferably radially, outwardly beyond the shank exterior surface and arranged for such vibratory movement in the direction of said longitudinal axis and has an internal fluid flow channel communicating with the shank passage and outwardly terminating in a mouth adjacent the scraper edge.

In this way, upon contacting the scraper edge against the undesired tissue in a direction crosswise of said longitudinal axis while subjecting the shank and tip to such vibratory movement in the direction of said longitudinal axis and to such accompanying flushing fluid flow via the tip mouth, the tissue will be effectively locally disintegrated and removed from the tissue site.

In particular, the shank and tip are integrally interconnected by an elbow like transition portion therebetween, and are both of tubular configuration.

The scraper edge favorably lies in a laterally, preferably radially, offset plane generally parallel to a longitudinal plane passing through said longitudinal axis, and is of generally ring shaped perimetric configuration in concentric relation to the tip lateral, preferably radial, axis and arranged to define the mouth of the tip channel. More specifically, the scraper edge may define a generally flat edge, or line edge, end surface in that offset plane.

According to another aspect of this invention, a combination is advantageously provided, comprising the tissue scraper element mounted on a hand held instrument via the base end portion of the element shank. The instrument contains a vibratory movement means operatively connected to the shank for imparting back and forth vibratory movement to the shank in the direction of its longitudinal axis at a selective amplitude and frequency, and the instrument is provided with an opening adjacent the shaft exterior surface, and a source of flushing fluid and a source of fluid suction, one of said sources being flow connected to the opening and the other of said sources being flow connected to the tip mouth.

Desirably, the instrument and tissue scraper element are sized for use in treating an eye, and the shaft and tip are sized for insertion through a corneal incision into the eye for extracting portions of the tissue of the natural eye lens.

According to a further aspect of this invention, a method of using the tissue scraper element is advantageously provided for extracting undesired tissue from a body tissue site.

The method comprises contacting the scraper edge against the undesired tissue, such as that of a cataracted natural eye lens, in a direction crosswise of said longitudinal axis while subjecting the shank and tip to back and forth vibratory movement of the shank and tip in the direction of said longitudinal axis sufficiently to disintegrate the tissue by mechanical vibratory contact of the scraper edge therewith, and while also subjecting the tissue site to accompanying flushing fluid flow via the tip mouth sufficiently to flush and remove the disintegrated tissue from the tissue site by such flow.

In particular, the subjecting of the tissue site to accompanying flushing fluid flow, includes supplying such fluid via the source of flushing fluid through one of said opening and said tip mouth sufficiently to flush the disintegrated tissue, and supplying such suction via the source of fluid suction through the other of said opening and said tip mouth sufficiently to remove the disintegrated tissue from the site.

Preferably, the subjecting of the tissue site to said flushing fluid flow, includes supplying such fluid via the source of flushing fluid through said opening sufficiently to flush the disintegrated tissue, and supplying such suction via the source of fluid suction through said tip mouth sufficiently to remove the disintegrated tissue from the site.

BRIEF DESCRIPTION OF THE DRAWINGS

Other objects of the invention will become apparent from the within specification and accompanying drawings, in which:

FIG. 1 is a schematic partial sectional view of a conventional hand held vibratory movement imparting and flushing fluid flow supplying instrument in which the tissue scraper element of the invention is mounted;

FIG. 2a is an enlarged schematic longitudinal sectional view of the round profile tissue scraper element of FIG. 1, showing details and relationships of pertinent parts;

FIG. 2b is a top view of said element shown in FIG. 2a;

FIG. 2c is a front elevational view of said element shown in FIG. 2a;

FIG. 3a is an enlarged schematic longitudinal section view, similar to the embodiment of FIGS. 2a, 2b and 2c, but of an oval profile tissue scraper element;

FIG. 3b is a top view of said element shown in FIG. 3a;

FIG. 3c is a transverse sectional view taken along line 3c—3c of FIG. 3b;

FIG. 4a is a view similar to FIG. 2a but of a further alternate form of the tissue scraper element in which the scraper edge is a convexly arranged pointed or linear edge;

FIG 4b is a view similar to FIG. 4a of a still further alternate form of said element in which the scraper edge is a concavely arranged pointed or linear edge;

FIG. 5 is a schematic view of an eye showing insertion of the instrument of FIG. 1 through a corneal incision thereinto for disintegration and removal of tissue of the natural lens by the tissue scraper element of the invention; and FIG. 6 is a schematic partial front elevational view of the eye showing the natural lens of the eye partially disintegrated and in doughnut form, indicating in solid line, and alternatively in phantom, two positions of the tissue scraper element of the invention used to disintegrate and remove tissue from different remote regions of the cataracted lens by mere rotation of the tool in the surgeon's hand.

DESCRIPTION OF THE PREFERRED EMBODIMENTS

Referring to the drawings, and initially to FIG. 1, a combination assembly 1 is shown of a known hand held vibratory motion imparting and flushing fluid supplying and removing instrument 2, e.g. as disclosed in said U.S. Pat. 3,589,363 to Banko and Kelman, having the tissue scraper element 3 of the invention, e.g. of about 1 mm external diameter, mounted therein, the parts being sized for use in treating an eye. The disclosure of said U.S. Pat. 3,589,363 is hereby incorporated herein in its entirety.

Instrument 2 is formed of a longitudinal housing 4 containing a conventional oscillator or vibrator 5, energized by power lines 6 and 7, and cooled by cooling fluid entering sealed rear chamber 8 via inlet hose 9 and leaving rear chamber 8 via outlet hose 10, lines 6 and 7 and hoses 9 and 10 being connected to appropriate sources, e.g. of electrical current and tap water, respectively, through service conduit 11.

Vibrator 5 is provided with a forward extension 12 mounted in housing 4 by a pair of axially spaced sealing rings 13,14 to define an annular sealed middle chamber 15 between housing 4 and vibrator extension 12, so as to flow communicate external suction line 16, which is connectable to a fluid suction source (not shown), with vibrator axial bore 17 leading from vibrator extension 12 completely through vibrator front end 18 on which tissue scraper element 3 of the invention is operatively mounted for back and forth longitudinal vibratory movement at a selective amplitude and frequency, e.g. about 0.003 inch amplitude and about 1,000 to 100,000 cycles per second frequency, and for fluid flow through the interior of element 3.

For this purpose, connector 19 releasably operatively connects the base end 20 of the longitudinal shank 21 of element 3 to vibrator front end 18, such that the front free end 22 of shank 21 protrudes a selective significant distance forwardly of housing 4 and ext ends along its longitudinal axis A which coincides with that of instrument vibrator 5.

According to the invention, free end 22 terminates in a unilateral sidewise offset or bent tip 23 which extends along a lateral, e.g. radial, axis B, crosswise of longitudinal axis A, tip 23 terminating in a laterally, e.g. radially, outwardly directed scraper edge 24. As is clear from FIG. 1, shank 21 and tip 23 are of constant and uniform diameter or girth throughout.

Flushing fluid line 25, which is connectable to a fluid supply source (not shown), e.g. saline solution, in conventional manner, flow communicates via housing front chamber 26 with housing front annular opening 27 to supply flushing fluid to the adjacent exterior surface 28 of shank 21, preferably after having first passed from opening 27 through an optional forwardly mounted resilient plastic sleeve 29 and out through the corresponding sleeve annular opening 30, to the region of the body tissue under treatment, sleeve 29 serving to protect the eye from undesired rubbing contact with the adjacent rigid surfaces of instrument 2 during its vibratory movement.

The flushing fluid flow exiting from opening 30 is eventually drawn in by suction through tip 23 into the interior of element 3 which communicates via axial bore 17 and line 16 with the suction source (not shown).

As is clear from FIGS. 2a, 2b and 2c, to achieve this purpose, shank 21 is provided with a longitudinal internal fluid flow passage 31, which communicates with axial bore 17 when element 3 is connected by connected 19 onto vibrator front end 18, and tip 23 is provided with an interior fluid flow channel 32 which communicates with shank passage 31 in the 90 degree elbow like transition portion defining a constant and uniform diameter or girth bend integrally interconnecting shank 21 and tip 23 (see FIG. 2a), channel 32 outwardly terminating in a mouth 33 adjacent scraper edge 24. Thus, shank 21 and tip 23 are conveniently both provided of constant and uniform diameter or girth tubular configuration.

In any case, scraper edge 24 is spaced laterally outwardly beyond shank exterior surface 28 and is arranged for such back and forth vibratory movement in the longitudinal direction of axis A, whereupon when scraper edge 24 is used to contact and disintegrate the undesired tissue, the remainder of element 3, i.e. the adjacent shank exterior surface 28, will not make contact with the tissue, thereby avoiding undesired disturbance of the delicate manipulations necessary for achieving the gentle, yet efficient, scraping disintegration action sought.

It will be seen from FIG. 2c that scraper edge 24 lies in a laterally, e.g. radially, offset plane P which is generally parallel to a longitudinal plane L passing through longitudinal axis A of shank 21 and instrument 2, and from FIG. 2b that scraper edge 24 is of generally curved or rounded ring shaped perimetric configuration in concentric relation to lateral, e.g. radial, axis B, being arranged to define mouth 33 of tip channel 32.

While tip 23, and in turn channel 32, mouth 33 and scraper edge 24, are of corresponding circular shape, as especially shown in FIGS. 2b and 2c, it will be seen from the alternative embodiment of FIGS. 3a, 3b and 3c, wherein like parts are assigned like reference numbers but with prime (') designations, that these parts may instead be of corresponding oval shape, as especially shown in FIGS. 3b and 3c. Of course, these parts may also be of other appropriate shape as desired, so long as the scraper edge in cooperation with the tip mouth function properly for the underlying purposes of element 3.

Also, while scraper edge 24 defines a generally flat edge end surface in offset plane P, i.e. a square cornered flat edge cross sectional shape, in the embodiment of FIGS. 2a, 2b and 2c, it will be seen that alternative shapes may instead be used such as line edge end surface shapes, i.e. pointed edge cross sectional shapes, as shown per scraper linear edge 24a in FIG. 4a and scraper linear edge 24b in FIG. 4b.

As shown in FIG. 5, the eyeball 50 includes the cornea 51, the iris 52 which forms the adjustable central pupil or opening 52a and which separates the anterior chamber 53 from the posterior chamber 54, and the natural eye lens 55, located by the zonules or suspensory ligament and fibers 56, attached to its periphery, in posterior chamber 54. Eye lens 55 is contained in lens capsule 57 which includes anterior wall 58, posterior wall 59 and cul-de-sac or peripheral groove 60.

As also shown in FIG. 5, in carrying out the tissue disintegration and removal procedure according to this invention, a corneal incision 61 is typically made of minimum length, e.g. about 3 mm to 6 mm, through which instrument 2 is inserted to place element 3 in desired position, i.e. via pupil 52a radially inwardly of iris 52, to attain safe access to lens 55 for contacting the tissue to be disintegrated and removed.

It will be realized that incision 61 is desirably kept as short in length as possible so as to minimize trauma to the patient, and thus its length is normally just sufficient for effecting the contemplated tissue removal procedures, e.g. for extracapsular removal of a cataracted natural eye lens, and, if called for, for receiving therethrough an intraocular lens to be implanted in the eye thereafter.

Use of the conventional straight-tip-type shank heretofore on instrument 2, operating by "jack-hammer-like" action axially against the tissue of the cataracted lens, served to break the tissue apart, but that use of such longitudinally acting "hammer" tip led to difficulties and awkwardness for the surgeon as earlier noted, whereas use of element 3 of the invention with its laterally offset tip 23 avoids these problems.

This may be seen from FIG. 6 wherein the solid line and phantom illustrations show how tip 23 may be more readily manipulated to contact tissue on different portions of the lens for more efficient disintegration and removal of the undesired lens tissue with minimal movement of the tip required by the surgeon. Given the offset location of incision 61 in eyeball 50 in relation to remote areas of the lens, and the fact that such remote areas can only be reached through pupil 52a as access opening, such rotational (about its longitudinal axis) movement of the tip permits the surgical procedure of cataract removal to be carried out with much greater speed. By a mere twist of the tool the surgeon can quickly move from one to another spaced region of the lens.

Specifically, relative to short incision 61 as pivot and within the circumferential limits of iris 52, the surgeon may not only move shank 21 longitudinally and angularly to place tip 23 at any areal point in capsule 57 (within the areal bounds of the capsule plane of FIG. 6) and at any crosswise width point therein (within the crosswise width bounds of the section plane of FIG. 5 or any other section plane through capsule 57), but also rapidly and easily twist or rock shank 21 about its axis at that, or any other, areal and width point to place scraper edge 24 at any localized spatial angular attitude among an essentially infinite number of attitudes (e.g. facing upwardly, downwardly, inwardly or outwardly) relative to any point within the volume confines of capsule 57.

This will permit precise vibrating contact with the pertinent tissue surface at that point, perpendicularly per tip axis B and longitudinally per shank axis A, at minimized risk of capsule puncture or other damage to the eye from such angular manipulations and vibrating movement of tip 23, unlike the above noted conventional instrument which is incapable of such localized infinite, rapid and easy change in spatial attitude of its straight "hammer tip38 by mere shank twisting by the surgeon and which lacks the ensuing instant advantages.

By reason of the laterally offset orientation of lateral axis B of tip 23 crosswise of longitudinal axis A of shank 21 and the outwardly directed orientation of scraper surface 24 along lateral axis B, plus the flat edge or cornered edge end surface 24 or 24' of FIG. 2a or FIG. 3a, or the line edge or pointed edge end linear surface 24a or 24b of FIG. 4a or FIG. 4b, as the case may be, upon contacting the scraper edge against the tissue in a direction crosswise of axis A while subjecting shank 21 and tip 23 to the back and forth vibratory movement per vibrator 5 in the direction of axis A, and to the accompanying flushing fluid flow via passage 31 and channel 32, the undesired tissue will be efficiently locally and uniformly scraped away and removed from the site.

Thus, tip 23, which is bent transversely relative to shank 21, moves in a back and forth vibratory path generally parallel to longitudinal axis A, enabling scraper edge 24 to be urged generally transversely, e.g. perpendicularly, to axis A and to the tissue surface, so as to contact safely and scrape away tissue by a milling or frictional type horizontal scraping action in a gradual and uniformly controlled manner for more precise, even and smooth one-step cleansing and removal of undesired tissue as finer individual particles, more readily flushed away by the fluid flow, and without fear of puncturing or otherwise damaging tissue intended to remain intact, such as posterior wall 59 and peripheral groove 60 (cf. FIGS. 5 and 6).

Moreover, such extracting of the undesired tissue using offset tip 23 on element 3 of the invention can be effected with comfortable handling and manipulation of the instrument by the surgeon.

These advantages of the invention are in direct contrast to the above described disadvantages of using the conventional instrument with its straight tip as disclosed for instance in said U.S. Pat. No. 3,589,363.

Among the most important advantages of the bent tip scraper element of the invention for removing a cataracted natural eye lens are (a) that it is possible to remove the hardest part of the natural lens, i.e. the cataracted nucleus, first, thereby permitting the hard nucleus to be kept out of contact with the cornea and in turn preventing scratching or like permanent damage to the cornea by such contact, (b) that it is possible to form a doughnut shape by removing the lens nucleus first and then easily break up the remaining softer outer portions of the lens tissue, (c) that the procedure is thereby faster, less wearing on the surgeon and safer for the patient, and (d) that the procedure lends itself to efficient endocapsular Phaco-Emulsification, in particular, by allowing such procedure to be performed efficiently through a tiny hole in the lens capsule into which the bent tip scraper element may be inserted.

It will be appreciated that when assembly 1 is used for treatment of the eye, all materials of element 3 and instrument 2 must be inert and compatible with the internal eye environment, and thus must be non-toxic as well as aseptic. The flushing fluid is preferably aseptic saline solution or the like, whereas tap water may be used for cooling vibrator 5 since rear chamber 8 of housing 4 is safely sealed off from the remainder of the unit. Of course, shank 21 and tip 23, and optional sleeve 29, must be sized for convenient insertion through a given minimum size corneal incision.

Use of sleeve 29 is preferred to soften the rubbing action of that portion of vibrating instrument 2 in contact with the corneal incision or any other adjacent portion of the eye, and thus minimize patient discomfort or trauma due to heat generation or otherwise.

While the above procedure has been described to provide for flushing fluid flow outwardly through sleeve opening 30 to the tissue site, and for return flow of such fluid and suspended or entrained disintegrated tissue therein via suction through tip mouth 33, tip channel 32 and shank passage 31, it will be understood that these flows may be reversed by connecting line 16 to a flushing fluid supply source and line 25 to a return suction source, as may be alternatively desired.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Tissue scraper element assembly for medical use in an eye for extracting undesired tissue from a cataracted natural eye lens by mechanical vibratory contact to disintegrate the tissue and by accompanying flushing fluid flow removal of the disintegrated tissue from the tissue site, which comprises a hand held instrument containing a vibratory movement means for imparting back and forth vibratory movement at a selective amplitude and frequency, and a tissue scraper element formed of a shank extending along a longitudinal axis and having a base end portion mounted on the hand held instrument and operatively connected to the vibratory movement means for back and forth vibratory movement of the shank in the direction of said longitudinal axis at such a selective amplitude and frequency, and a free end portion terminating in a unilateral sidewise offset tip ex tending along a lateral axis crosswise of said longitudinal axis, the shank having an exterior surface and an internal fluid flow passage, and the tip terminating in a laterally outwardly directed scraper edge spaced laterally outwardly beyond the shank exterior surface and arranged for such vibratory movement in the direction of said longitudinal axis and having an internal fluid flow channel communicating with the shank passage and outwardly terminating in a mouth adjacent and surrounded by the scrapper edge, said scrapper edge comprising means for disintegrating tissue from the tissue site, the scraper edge, the instrument being provided with an opening adjacent the shank exterior surface, a first flow path connectable to a source of flushing fluid and a second flow path connectable to a source of fluid suction, one of said flow paths being flow connected to the opening and the other of said flow paths being flow connected to the tip mouth via the shank passage and tip channel, the instrument and tissue scraper element being sized for use in treating the cataracted lens in an eye, and the shaft and tip being sized for insertion through a corneal incision and the central opening of the iris into the posterior chamber of the eye and further through an incision in the lens capsule located in the posterior chamber for extracting portions of the tissue of the natural eye lens disposed in the lens capsule, whereby upon connecting the first flow path to a source of flushing fluid and the second flow path to a source of fluid suction, and upon contacting the scraper edge against the undesired tissue in a direction crosswise of said longitudinal axis while subjecting the shank and tip to such vibratory movement in the direction of said longitudinal axis and to such accompanying flushing fluid flow, including supplying such fluid via the source of flushing fluid through one of said opening and said tip mouth and such suction via the source of fluid suction through the other of said opening and said tip mouth, such tissue will be effectively locally disintegrated and removed from the tissue site.

2. Assembly of claim 1 wherein the shank and tip are of constant diameter and integrally interconnected by an elbow like transition portion defining a constant diameter bend of about 90 degrees therebetween.

3. Assembly of claim 1 wherein the shank and tip are of constant diameter tubular configuration.

4. Assembly of claim 1 wherein the scraper edge lies in a laterally offset plane generally parallel to a longitudinal plane passing through said longitudinal axis.

5. Assembly of claim 1 wherein the lateral axis is a generally radial axis, and the scraper edge is generally radially outwardly directed, lies in a radially outwardly offset plane generally parallel to a longitudinal plane passing through said longitudinal axis, is of generally curved ring shaped perimetric configuration in concentric relation to said radial axis, and is arranged to define the mouth of the tip channel.

6. Assembly of claim 1 wherein the scraper edge is of generally curved ring shaped perimetric configuration in concentric relation to said lateral axis and arranged to define the mouth of the tip channel.

7. Assembly of claim 6 wherein the scraper edge defines a flat edge end surface in said offset plane.

8. Assembly of claim 6 wherein the scraper edge defines a line edge end surface in said offset plane.

9. Method of using the assembly of claim 1 for extracting undesired tissue from a cataracted natural eye lens, comprising inserting the shank and tip of said scraper element longitudinally through a corneal incision and the central opening of the iris into the posterior chamber of an eye and further through an incision in the lens capsule located in the posterior chamber and in which the natural eye lens is disposed, such that the longitudinal axis of the shank extends in longitudinal alignment with the corneal incision, the central opening of the iris and the incision in the lens capsule and the shank is pivotally movable relative to the corneal incision as pivot point under the limiting constraints of said longitudinal alignment for limited movement of the tip in a direction crosswise of the direction of said longitudinal alignment yet permitting rotation of the shank and tip about said longitudinal axis, and contacting the scraper edge against the undesired tissue of the eye lens in a direction crosswise of said longitudinal axis while subjecting the shank and tip to back and forth vibratory movement of the shank and tip in the direction of said longitudinal axis and to rotation about said longitudinal axis sufficiently to disintegrate the tissue by mechanical vibratory contact of the scraper edge therewith, and while also subjecting the tissue site to accompanying flushing fluid flow, including supplying such fluid via the source of flushing fluid through one of said opening and said tip mouth sufficiently to flush the disintegrated tissue, and supplying such suction via the source of fluid suction through the other of said opening and said tip mouth sufficiently to remove the disintegrated tissue from the tissue site.

10. Method of claim 9 wherein the fluid is supplied via the source of flushing fluid through said opening and the suction is supplied via the source of fluid suction through said tip mouth.

* * * * *